United States Patent
Higuchi et al.

(10) Patent No.: US 9,034,789 B2
(45) Date of Patent: May 19, 2015

(54) ADSORPTION CARBON, AND ADSORBENT

(75) Inventors: Masato Higuchi, Shizuoka (JP); Takao Kimura, Ishikawa (JP); Masayoshi Takeuchi, Toyama (JP); Kisaburo Deguchi, Ishikawa (JP)

(73) Assignee: DISEASE ADSORPTION SYSTEM TECHNOLOGIES CO., LTD., Ishikawa (JP)

(*) Notice: Subject to any disclaimer, the term of this patent is extended or adjusted under 35 U.S.C. 154(b) by 182 days.

(21) Appl. No.: 13/583,181

(22) PCT Filed: Mar. 2, 2011

(86) PCT No.: PCT/JP2011/054714
§ 371 (c)(1),
(2), (4) Date: Sep. 6, 2012

(87) PCT Pub. No.: WO2011/111577
PCT Pub. Date: Sep. 15, 2011

(65) Prior Publication Data
US 2013/0040812 A1  Feb. 14, 2013

(30) Foreign Application Priority Data
Mar. 10, 2010 (JP) .................. 2010-053604

(51) Int. Cl.
B01J 20/20 (2006.01)
A61K 33/44 (2006.01)
B01J 20/28 (2006.01)
B01J 20/30 (2006.01)

(52) U.S. Cl.
CPC ............. *A61K 33/44* (2013.01); *B01J 20/20* (2013.01); *B01J 20/28069* (2013.01); *B01J 20/3078* (2013.01); *B01J 20/2808* (2013.01)

(58) Field of Classification Search
CPC .... A61K 33/44; B01J 20/20; B01J 20/28069; B01J 20/2808; B01J 20/3078
USPC .................. 423/445 R; 502/416, 417
See application file for complete search history.

(56) References Cited

U.S. PATENT DOCUMENTS

| 7,585,132 B2 * | 9/2009 | Imbrie ............... 405/128.75 |
| 2004/0141963 A1 | 7/2004 | Umekawa et al. |
| 2008/0107589 A1 | 5/2008 | von Blucher et al. |

(Continued)

FOREIGN PATENT DOCUMENTS

| DE | 202006016898 U1 | 12/2007 |
| EP | 1440692 | 7/2004 |
| JP | 56-73542 A | 6/1981 |

(Continued)

OTHER PUBLICATIONS

Machine English translation of JP2004-244414.*

(Continued)

*Primary Examiner* — Richard M Rump
(74) *Attorney, Agent, or Firm* — Hoffmann & Baron, LLP

(57) ABSTRACT

Provided are an adsorptive carbon which can effectively adsorb vivotoxins such as advanced glycation end products (AGEs), and an adsorbent containing the adsorptive carbon as an active ingredient. The adsorptive carbon according to the present invention has a total pore volume of 0.10 to 1.0 mL/g, an average pore diameter of 1.0 to 2.0 nm, and an absorbance of an infrared absorption band at 1650-1800 $cm^{-1}$ of no less than 0.005.

4 Claims, 3 Drawing Sheets

(56) References Cited

U.S. PATENT DOCUMENTS

2009/0159091 A1 6/2009 Karles et al.
2010/0214722 A1 8/2010 Fujii et al.

FOREIGN PATENT DOCUMENTS

| | | |
|---|---|---|
| JP | 62-11611 B2 | 3/1987 |
| JP | H03242310 A | 10/1991 |
| JP | 2001-122608 A | 5/2001 |
| JP | 2001-287905 | 10/2001 |
| JP | 2002-104816 A | 4/2002 |
| JP | 2002-253649 A | 9/2002 |
| JP | 2002-308785 A | 10/2002 |
| JP | 2003242310 A | 8/2003 |
| JP | 2004-123673 A | 4/2004 |
| JP | 2004-244414 A | 9/2004 |
| JP | 2004-315242 | 11/2004 |
| JP | 2006-36734 A | 2/2006 |
| JP | 2006-111604 A | 4/2006 |
| JP | 2007-197338 A | 8/2007 |
| JP | 2008-303193 A | 12/2008 |
| JP | 2009-13012 A | 1/2009 |
| JP | 2009-013012 A | 1/2009 |
| WO | 2004/099073 A2 | 11/2004 |
| WO | 2005/060980 A1 | 7/2005 |

OTHER PUBLICATIONS

Extended European Search Report issued to EP Application No. 11753236.6, mailed Jul. 22, 2013.

Office Action issued to CN Application No. 201180012656.X, mailed Apr. 25, 2014.

Yang Zhen Jing, et al., "Studies in production of novel activated carbon from plant cellulose materials", Journal of Chemical Industry of Forest Products, 1996, vol. 2., pp. 3-6, By relevancy in trans OA only.

Takeuchi, Masayoshi et al., "Detection of Noncarboxymethyllysine and Carboxymethyllysine Advanced Glycation End Products (AGE) in Serum of Diabetic Patients", Molecular Medicine, vol. 5, No. 6, pp. 393-405, 1999.

Yoshida, Hisayoshi et al., "Fourier Transform Infrared Spectra of Activated Carbons", Tanso, No. 111, pp. 149-153, 1982.

International Search Report issued for Application No. PCT/JP2011/054714, mailed on Jun. 7, 2011.

Tennison, S.R., "Phenolic-resin-derived activated carbons"—Applied Catalysis A: General 173 (1998) 289-311, Mast Carbon Ltd., Henley Park, Guildford GU3 2AF, UK.

Sevilla, M., Fuertes, A.B., "The production of carbon materials by hydrothermal carbonization of cellulose"—ScienceDirect, Carbon 47 (2009) 2281-2289, Instituto Nacional del Carbon (CSIC), Oviedo, Spain.

* cited by examiner

ADSORPTION CARBON, AND ADSORBENT

CROSS-REFERENCE TO RELATED APPLICATION

This application is the National Stage of International Application No. PCT/JP2011/054714, filed Mar. 2, 2011, which claims the benefit of Japanese Application No. 2010-053604, filed Mar. 10, 2010, the entire contents of all of which are incorporated by reference herein.

FIELD OF INVENTION

The present invention relates to an adsorptive carbon which can effectively adsorb vivotoxin, and an adsorbent containing the adsorptive carbon as an active ingredient.

BACKGROUND OF THE INVENTION

It is known that most vivotoxins are produced and absorbed within the intestines, migrate into the blood, and provide a cause of organ disorders. Normally, the vivotoxins are detoxified in the liver, and excreted by the kidney. However, patients suffering from reduced renal function or liver function cannot excrete the vivotoxins due to these organ dysfunctions, and accumulate the vivotoxins within the body, which occasionally leads to the presentation of severe symptoms such as uremia and disturbance of consciousness. Due to the increase in lifestyle diseases including diabetes mellitus, the number of patients suffering from renal dysfunction or hepatic dysfunction increases every year, and therefore the development of medical devices substituting organ functions or therapeutic agents for compensating these organ dysfunctions and removing the vivotoxins from the body, and the development of therapeutic agents or food products for suppressing the absorption of the vivotoxins from the intestines to the blood are important challenges.

Currently, hemodialysis is the most prevailing method for removing the vivotoxins; basically, this methodology is based on size fractionation, and therefore, the removal of disease-causing molecules such as vivotoxins adsorbed to albumin and β2 microglobulin by means of the hemodialysis has been difficult.

In addition, in recent years, much attention has been paid to dialysis therapy in which dialysates of the hemodialysis are purified, regenerated and recycled, and wearable dialysis. For these therapies to gain widespread use, a technology is required for efficiently removing the vivotoxins that have migrated from the blood to the dialysates during the hemodialysis.

On the other hand, an activated carbon (adsorptive carbon) for oral administration is listed in the Japanese Pharmacopoeia as a medicinal carbon and the like, and has been utilized at the time of drug poisoning and food poisoning for the purpose of causing toxic substances to be adsorbed thereon in the gastrointestinal organs and to be excreted as stools. In addition to the detoxification of the drug poisoning cases as described above, administration of the activated carbon to patients suffering from reduced renal function enables a reduction in the burden placed on the kidney, a delay in the timing of the introduction of hemodialysis, and a reduction in the frequency of the dialysis. Orally-administrable activated carbon formulations will offer numerous benefits, since the hemodialysis places considerable mental, physical, and economic burden on patients.

As the activated carbon formulations for oral administration, substances which are obtained by using pitch such as petroleum pitch, and phenolic resins as a carbonaceous raw material, and calcinating the carbonaceous raw material with non-flammable gases are known (see, Patent Documents 1 to 7 and the like). These activated carbon formulations have several advantages, including high stability and high safety to living organisms and reduced side effects such as constipation, and are commercially available as fine granules and capsules, for example, under the trade name "Kremezin" (registered).

Patent Document 1: Japanese Examined Patent Application, Publication No. 62-11611

Patent Document 2: Japanese Unexamined Patent Application, Publication No. 2002-253649

Patent Document 3: Japanese Unexamined Patent Application, Publication No. 2002-308785

Patent Document 4: Japanese Unexamined Patent Application, Publication No. 2004-244414

Patent Document 5: Japanese Unexamined Patent Application, Publication No. 2004-123673

Patent Document 6: Japanese Unexamined Patent Application, Publication No. 2006-36734

Patent Document 7: Japanese Unexamined Patent Application, Publication No. 2008-303193

Non-Patent Document 1: Takeuchi M. et al., Mol. Med 5: 393-405 (1999)

SUMMARY OF THE INVENTION

Problems to be Solved by the Invention

In recent years, a possibility is suggested that due to change in eating habits, toxins derived from new food products, such as advanced glycation end products (AGEs) are absorbed into the blood, and cause a variety of organ disorders (see, non-Patent Document 1 and the like).

Thus, adsorptive removal of the advanced glycation end products with the activated carbon formulations is desired; however, conventional activated carbon formulations such as Kremezin (registered) have only low absorptive ability toward the advanced glycation end products.

The present invention was developed in view of the above-mentioned conventional problems. An object of the present invention is to provide an adsorptive carbon which can effectively adsorb vivotoxin such as the advanced glycation end products, and an adsorbent containing the adsorptive carbon as an active ingredient.

Means for Solving the Problems

The present inventors have pursued intensive studies for the purpose of solving the problems. As a result, the present inventors have found that the adsorptive carbon with which the above-mentioned problems can be solved is obtained by regulating calcination conditions and thereby controlling pore structures of the adsorptive carbon and the like, to accomplish the present invention. More particularly, the present invention is as follows.

In a first aspect of the present invention, an adsorptive carbon is provided which has a total pore volume of 0.10 to 1.0 mL/g, an average pore diameter of 1.0 to 2.0 nm, and an absorbance of an infrared absorption band at 1650-1800 $cm^{-1}$ of no less than 0.005.

In a second aspect of the present invention, the adsorptive carbon according to the first aspect is provided, in which the adsorptive carbon is produced by calcinating a carbonaceous raw material with an electric furnace.

In a third aspect of the present invention, the adsorptive carbon according to the second aspect is provided, in which the carbonaceous raw material is a high purity cellulose of no less than 90% purity.

In a fourth aspect of the present invention, the adsorptive carbon according to the second or third aspect is provided, in which the carbonaceous raw material is a cellulose particulate or a cellulosic nonwoven fabric.

In a fifth aspect of the present invention, an adsorbent is provided which contains the adsorptive carbon according to any one of the first to fourth aspects as an active ingredient.

Effects of the Invention

According to the present invention, an adsorptive carbon which can effectively adsorb vivotoxins such as the advanced glycation end products, and an adsorbent containing the adsorptive carbon as an active ingredient can be provided.

Figure 1:
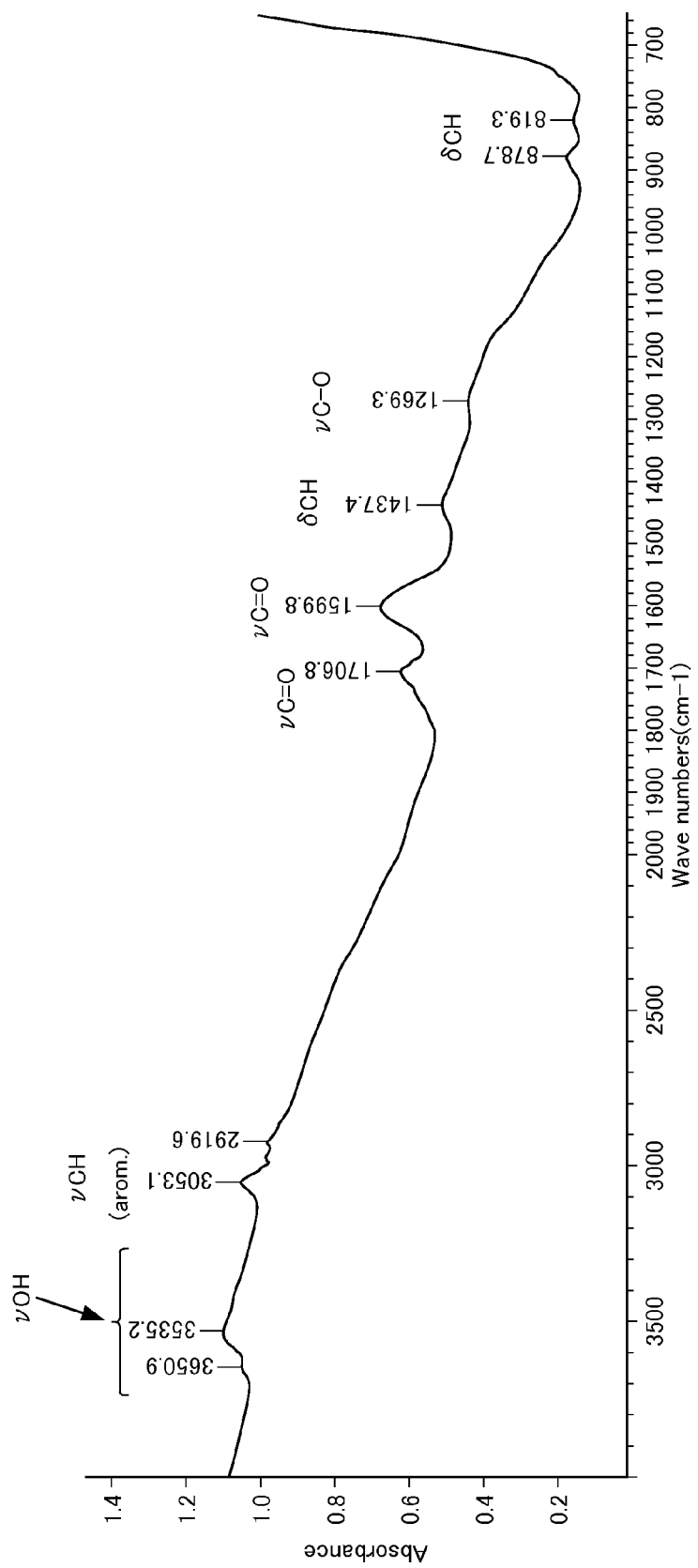
FIG. 1 is a chart showing an infrared absorption spectrum of the adsorptive carbon according to Example 2.

DETAILED DESCRIPTION OF THE INVENTION (Adsorptive Carbon)

The adsorptive carbon according to the invention is characterized in that the adsorptive carbon has a total pore volume of 0.10 to 1.0 mL/g, an average pore diameter of 1.0 to 2.0 nm, and an absorbance of an infrared absorption band at 1650-1800 $cm^{-1}$ of no less than 0.005.

The total pore volume can be calculated from the amount of $N_2$ adsorbed when replaced with liquid nitrogen at a relative pressure of 0.98, by applying Gurvitsch rule. Moreover, the average pore diameter can be calculated from BET method specific surface area and the total pore volume, according to the following formula:

$$\text{average pore diameter (nm)} = \left( \frac{\text{total pore volume (mL/g)}}{\text{BET method specific surface area (m}^2\text{/g)}} \right) \times 4 \times 1000$$

As a carbonaceous raw material which can be used as a raw material for the adsorptive carbon according to the invention include known raw materials, for example, sawdust, woods, coconut shells, oil carbon, phenolic resins, celluloses, acrylonitrile, coal pitch, petroleum pitch and the like.

Among these raw materials, substantially phosphorus- and potassium-free, high purity celluloses of no less than 90% purity are preferable, and high purity celluloses of purity of no less than 95% are more preferable. Materials for the high purity celluloses include known materials, for example, cuprammonium rayon, viscose rayon, cotton, pulp, linter, polynosic, lyocell (tencel) and the like.

In particular, when the adsorptive carbon according to the invention is used as an oral adsorbent, cellulose particulates are preferably used as the carbonaceous raw material, and cellulose particulates with particle size of 0.1 to 1000 μm are more preferably used.

Furthermore, when the adsorptive carbon according to the invention is used in the purification of the blood and dialysates, cellulosic nonwoven fabrics are preferably used as the carbonaceous raw material, and cellulosic nonwoven fabrics in which each fiber has a single fiber fineness of 0.1 to 3 dtex are more preferably used. In addition, for the purification of the blood and the dialysates, string-like cellulosic materials and woven fabric cellulosic materials are also preferably used.

In order to produce the adsorptive carbon according to the present invention, the above-mentioned carbonaceous raw material is calcinated with an electric furnace or the like. Conventionally, for obtaining adsorptive carbons, carbonaceous raw materials are generally calcinated with non-flammable gases; in contrast, in the present invention, the carbonaceous raw material is calcinated with the electric furnace or the like, in the absence of the gases. This procedure can afford the adsorptive carbon having the above-mentioned pore structures and the like.

In addition, because the gases are not used, when non-woven fabric, string-like, or woven fabric cellulosic materials as mentioned above are employed as the carbonaceous material, adsorptive carbons that maintain the respective structures of the original cellulosic materials can be obtained. Accordingly, the adsorptive carbons thus obtained are useful in the purification of the blood and the dialysates.

A calcination temperature of 300 to 1500° C. is preferable. In the calcination, the calcination temperature is not raised continuously to the final calcination temperature, but raised in stages. Specifically, the calcination temperature is first raised to 300 to 500° C. at a rate of 10 to 100° C. per hour, and maintained at that temperature for 1 to 6 h. Subsequently, the calcination temperature is raised at a rate of 10 to 100° C. per hour, and maintained for 1 to 6 h for every increase in temperature of 100 to 500° C.

By using the adsorptive carbon thus obtained, the vivotoxins can be effectively adsorbed and removed. The vivotoxins that can be adsorbed and removed include substances which are metabolically produced from carbohydrates and proteins and the like within the body, substances which are taken orally along with foods, and more specifically, advanced glycation end products, indole, indoxylsulfuric acid, hydrogen sulfide, ammonia, p-cresol, dioxin, urea, creatinine and the like.

(Adsorbent)

The adsorbent according to the invention is an adsorbent which contains the adsorptive carbon according to the invention as an active ingredient. The adsorbent may be used in medical care applications, or in other applications such as dietary supplements. The adsorbent can be in the form of powders, granules, tablets, sugar coated tablets, capsules, suspensions, sticks, divided packages, emulsions and the like.

For example, in the case of the tablets, the adsorptive carbon according to the invention is blended with additives such as binders, excipients, lubricants, coloring agents, disintegrants, and oxygen scavengers, and then formed into tablets by a routine method.

A dosage or dose of the adsorbent varies depending on the subject in need thereof (human or other animal), age, individual difference, disease condition and the like; when the subject is a human, the oral dosage is generally 1 to 20 g of the adsorbent per day, in which the daily dosage may be divided into three to four portions, and may be further increased or decreased appropriately with the disease condition.

EXAMPLES

In the following, Examples of the present invention will be illustrated, but the scope of the present invention is by no means limited thereto.

In the following Examples, the total pore volume and the average pore diameter of the adsorptive carbon, and the infrared absorption spectra of the adsorptive carbon were measured in the following manner.

(Measurement of Total Pore Volume and Average Pore Diameter)

About 0.1 g of the adsorptive carbon was taken in a standard cell, and subjected to a degassing treatment (drying at reduced pressures) in a pretreatment unit of Shimadzu-Micrometrics ASAP 2010 at a temperature of about 200° C. for about 15 h, and then the total pore volume and the average pore diameter were measured with the apparatus ($N_2$ gas adsorption method, specific surface area/pore distribution measurement). For the adsorptive carbon in the form of nonwoven fabric, the measurement was carried out after cutting the nonwoven fabric. The total pore volume was calculated at a relative pressure of 0.98, and the average pore diameter was calculated from BET method specific surface area and the total pore volume. The results are shown in respective Example or Comparative Example section.

(Measurement of Infrared Absorption Spectra of Adsorptive Carbon)

Analysis was carried out with a Fourier transform infrared spectrophotometer (from Varian Technologies Japan Ltd.). Conditions for microinfrared spectroscopy are as follows.

Measurement was carried out via a transmission mode under the following condition: an aperture size of 100×100 μm, number of scans of 100, measuring wavenumber range of 4000 to 650 $cm^{-1}$, an MCT detector, and a resolution of 4 $cm^{-1}$. The adsorptive carbon was mounted on a stage for microIR analysis (Ge crystal plate), and spread into a thin layer with a collection needle so that infra-red light could transmit through the thin layer of the adsorptive carbon, and infrared absorption spectra were measured. In the measurements, no saturation of the infrared absorption spectra was confirmed within the measuring wavenumber range. The absorbance of an infrared absorption band was calculated by utilizing a slope of the baseline characteristic to inorganic materials, and employing the absorbance at 4000 $cm^{-1}$ as a reference. However, since the shape of the baseline characteristic to inorganic materials may vary depending on the form of the samples, infrared absorption spectra were measured quintuply (i.e., n=5), the respective absorbance values were calculated, and the averaged absorbance value were taken as the measured absorbance value. The results are shown in respective Example or Comparative Example section.

Example 1

One hundred g of CEOLUS (registered) PH-101 (from Asahi Kasei Chemicals Corp., an average particle size of 50 μm) were charged into a crucible, and calcinated in an electric furnace to prepare an adsorptive carbon. The calcination condition was as follows.

The temperature of the electric furnace is raised to 300° C. at a rate of 50° C. per hour, and maintained at 300° C. for 1 h and 30 min.

Then, the temperature is raised to 600° C. at the same rate, and maintained at 600° C. for 2 h.

Subsequently, the temperature is raised to 800° C. at the same rate, and maintained at 800° C. for 2 h.

Subsequently, the temperature is raised to 1000° C. at a rate of 30° C. per hour, and maintained at 1000° C. for 2 h.

Subsequently, the temperature is raised to 1200° C. at a rate of 25° C. per hour, and maintained at 1200° C. for 2 h.

Furthermore, the temperature is raised to 1300° C. at a rate of 20° C. per hour, and maintained at 1300° C. for 3 h.

Finally, the temperature of the electric furnace is lowered to 1000° C. over 7 h, then to 800° C. over 4 h, and subsequently the electric furnace is left to cool naturally.

In the resulting adsorptive carbon, the total pore volume was 0.723 mL/g, the average pore diameter was 1.7 nm, and the absorbance of an infrared absorption band at 1650 to 1800 $cm^{-1}$ in the Fourier transform infrared spectroscopy was 0.006.

Example 2

One hundred g of CEOLUS (registered) PH-101 (from Asahi Kasei Chemicals Corp., an average particle size of 50 μm) were charged into a crucible, and calcinated in an electric furnace to prepare an adsorptive carbon. The calcination condition was as follows.

The temperature of the electric furnace is raised to 300° C. at a rate of 20° C. per hour, and maintained at 300° C. for 5 h and 30 min.

Then, the temperature is raised to 500° C. at a rate of 15° C. per hour, and maintained 500° C. for 4 h.

Finally, the electric furnace is left to cool naturally.

In the resulting adsorptive carbon, the total pore volume was 0.188 mL/g, the average pore diameter was 1.8 nm, and the absorbance of an infrared absorption band at 1650 to 1800 $cm^{-1}$ in the Fourier transform infrared spectroscopy was 0.086. The infrared absorption spectrum of the adsorptive carbon according to Example 2 is shown in FIG. 1.

Example 3

One hundred g of CEOLUS (registered) PH-101 (from Asahi Kasei Chemicals Corp., an average particle size of 50 μm) were charged into a crucible, and calcinated in an electric furnace to prepare an adsorptive carbon. The calcination condition was as follows.

The temperature of the electric furnace is raised to 300° C. at a rate of 25° C. per hour, and maintained at 300° C. for 2 h and 30 min.

Then, the temperature is raised to 600° C. at the same rate, and maintained at 600° C. for 4 h.

Subsequently, the temperature is raised to 800° C. at the same rate, and maintained at 800° C. for 3 h.

Furthermore, the temperature is raised to 1000° C. at the same rate, and maintained at 1000° C. for 3 h.

Finally, the temperature of the electric furnace is lowered to 800° C. over 4 h, and subsequently the electric furnace is left to cool naturally.

In the resulting adsorptive carbon, the total pore volume was 0.407 mL/g, the average pore diameter was 1.7 nm, and the absorbance of an infrared absorption band at 1650 to 1800 $cm^{-1}$ in the Fourier transform infrared spectroscopy was 0.007.

Example 4

One hundred g of BEMLIESE SC282 (from Asahi Kasei Fibers Corp.; a single fiber fineness of the fiber was 1.5 dtex)

were charged into a crucible, and calcinated in an electric furnace to prepare an adsorptive carbon. The calcination condition was as follows.

The temperature of the electric furnace is raised to 300° C. at a rate of 50° C. per hour, and maintained at 300° C. for 1 h and 30 min.

Then, the temperature is raised to 600° C. at the same rate, and maintained at 600° C. for 2 h.

Subsequently, the temperature is raised to 800° C. at the same rate, and maintained at 800° C. for 2 h.

Subsequently, the temperature is raised to 1000° C. at a rate of 30° C. per hour, and maintained at 1000° C. for 2 h.

Furthermore, the temperature is raised to 1200° C. at a rate of 25° C. per hour, and maintained at 1200° C. for 3 h.

Finally, the temperature of the electric furnace is lowered to 1000° C. over 5 h, then to 800° C. over 4 h, and subsequently the electric furnace is left to cool naturally.

In the resulting adsorptive carbon, the total pore volume was 0.854 mL/g, the average pore diameter was 1.9 nm, and absorbance of an infrared absorption band at 1650 to 1800 $cm^{-1}$ in the Fourier transform infrared spectroscopy was 0.062.

Comparative Example 1

Kremezin (registered) (from Kureha Chemical Industry Co., Ltd.), a commercially available adsorptive carbon for medical care, was used as received.

The total pore volume was 0.784 mL/g, the average pore diameter was 1.9 nm, and the absorbance of an infrared absorption band at 1650 to 1800 $cm^{-1}$ in the Fourier transform infrared spectroscopy was 0.004.

(Adsorption Experiment on Advanced Glycation End Products (AGEs))

To 0.1 g of the adsorptive carbon in respective tubes was added 1 mL (140 U) of glucose-derived AGE (AGE-1) diluted with 50 mM phosphate buffer (pH 7.4), and the tubes were rotated with a tube rotator at 37° C. for 3 h, to cause AGE-1 to be adsorbed to the respective adsorptive carbons. Subsequently, the respective mixtures were centrifuged at 10,000 rpm for 10 min to collect the supernatant.

Then, the amount of AGE-1 in the supernatant was determined via a competitive ELISA method using AGE-1-BSA and anti-AGE-1 antibody, and the amounts of AGE-1 in the absence and presence of the adsorptive carbon were compared to calculate the adsorption rate (%).

The quantitative determination of AGE-1 by means of the competitive ELISA method was carried out according to the following method.

First, AGE-1-BSA was dissolved in a coating liquid so as to prepare a 1 μg/mL solution, and 100 μL of the solution was added to each well of a 96-well high bind EIA/RIA microplate, to allow AGE-1-BSA to be adsorbed overnight at 4° C. and to be solid phased. Then, a plate washer (Auto mini washer, Model AMW-8) was used to wash the microplate three times with a washing liquid, and 200 μL of a blocking solution was added to each well, and the mixture was incubated at room temperature for 1 h to effect blocking. Furthermore, after washing three times with the washing liquid, to each well were added 50 μL of the supernatant diluted with a dilution buffer and 50 μL of AGE-1 antibody diluted with the dilution buffer containing 1 mg/mL BSA, and the mixture was incubated at 30° C. for 2 h with shaking.

Subsequently, the microplate was washed with the washing liquid three times, and 100 μL of alkaline phosphatase (AP)-labelled sheep anti-rabbit IgG antibody diluted with the dilution buffer was added to each well, and the mixture was incubated at 37° C. for 1 h. After washing three times with the washing liquid, 100 μL of AP substrate kit solution was added, and the mixture was incubated at 37° C. for about 1 h, and then an absorbance at 405 nm was measured with a microplate reader (Labsystems multiskan ascent, Model No. 354). The amount of AGE-1 in the respective supernatants was calculated based on the calibration curve for AGE-1-BSA.

It should be noted that the amount of AGEs corresponding to 1 μg of AGE-1-BSA standard was defined as 1 U.

The compositions of the coating liquid, the blocking solution, and the dilution buffer used in the above-mentioned experiment are as follows:

Coating liquid: a solution containing sodium carbonate, sodium bicarbonate, 0.05% sodium azide (pH 9.6 to 9.8);

Blocking solution: a phosphate buffered saline containing 1% BSA, 0.05% sodium azide (pH 7.4); and Dilution buffer: 50 mM 2-amino-2-hydroxymethyl-1,3-propanediol[tris(hydroxymethyl)aminomethane] buffer containing 0.1% glycerol, 0.1% Tween 20, 0.05% sodium azide (pH 7.4).

Figure 2:
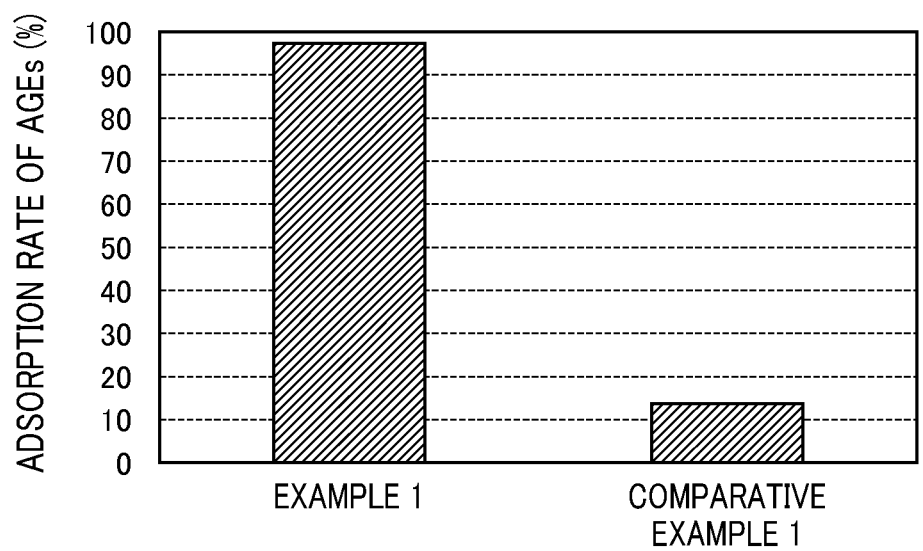
FIG. 2 is a graph showing the results of the adsorption experiments on the advanced glycation end products, using the adsorptive carbons according to Example 1 and Comparative Example 1.

The results from the adsorptive carbons according to Example 1 and Comparative Example 1 are shown in FIG. 2. As shown in FIG. 2, the adsorptive carbon according to Example 1 was able to adsorb 97.4% of the AGE-1, whereas the adsorptive carbon according to Comparative Example 1 was able to adsorb only 13.8% of the AGE-1. It can be seen from the results that the adsorptive carbon according to Example 1 can adsorb and remove AGE-1 more effectively than the adsorptive carbon according to Comparative Example 1.

(Adsorption Experiment on Serum Containing Vivotoxins)

To 50 mg of the adsorptive carbon in respective tubes were added 0.5 mL of a serum of a hemodialysis patient, and the tubes were rotated with a tube rotator at room temperature for 3 h. Subsequently, the respective mixtures were centrifuged at 10,000 rpm for 10 min to collect the supernatant.

Then, concentrations of albumin (ALB), urea nitrogen (BUN), creatinine (Cre), sodium (Na), potassium (K), chlorine (Cl), inorganic phosphorus (IP), total cholesterol (T-CHO), and triglycerides (TG) in the supernatant were determined with Hitachi autoanalyzer.

The results from the adsorptive carbons according to Example 3 and Comparative Example 1 are shown in Table 1 below. As shown in Table 1, the adsorptive carbon according to Example 1 was able to selectively remove urea and creatinine without affecting ALB, Na, K, Cl, IP, T-CHO, and TG, all of which are responsible for homeostasis of living organisms. In addition, it has been demonstrated that in urea removing property, the adsorptive carbon according to Example 3 has higher performance than the adsorptive carbon according to Comparative Example 1.

TABLE 1

|  | renal failure serum before dialysis | Example 3 | renal failure serum before dialysis | Comparative Example 1 |
|---|---|---|---|---|
| ALB | 3.7 | 3.8 | 3.6 | 3.5 |
| BUN | 63.1 | 33.2 | 67.3 | 38.5 |
| Cre | 10.13 | 0.03 | 10.49 | 0.03 |
| Na | 138 | 135 | 136 | 138 |
| K | 5.1 | 4.6 | 5 | 5 |
| Cl | 103 | 102 | 99 | 98 |
| IP | 5.2 | 5.2 | 5.1 | 5.2 |
| T-CHO | 160 | 158 | 163 | 173 |
| TG | 85 | 81 | 107 | 117 |

(Adsorption Experiment on Indoxylsulfuric acid)

To 50 mg of the adsorptive carbon in respective tube was added 0.5 mL of a serum of a healthy human supplemented with indoxylsulfuric acid at a concentration of 20 μg/mL, and the tubes were rotated with a tube rotator at room temperature for 5 min, to cause 3-indoxylsulfuric acid to be adsorbed to the respective adsorptive carbons. Subsequently, the respective mixtures were centrifuged at 10,000 rpm for 10 min to collect the supernatant.

After the supernatant was deproteinized with 4% trichloroacetic acid solution, the concentration of 3-indoxylsulfuric acid was determined with a liquid chromatograph-mass spectrophotometer (LC-MS/MS). In this experiment, an identical but adsorptive carbon-free run was employed as a control.

Figure 3:
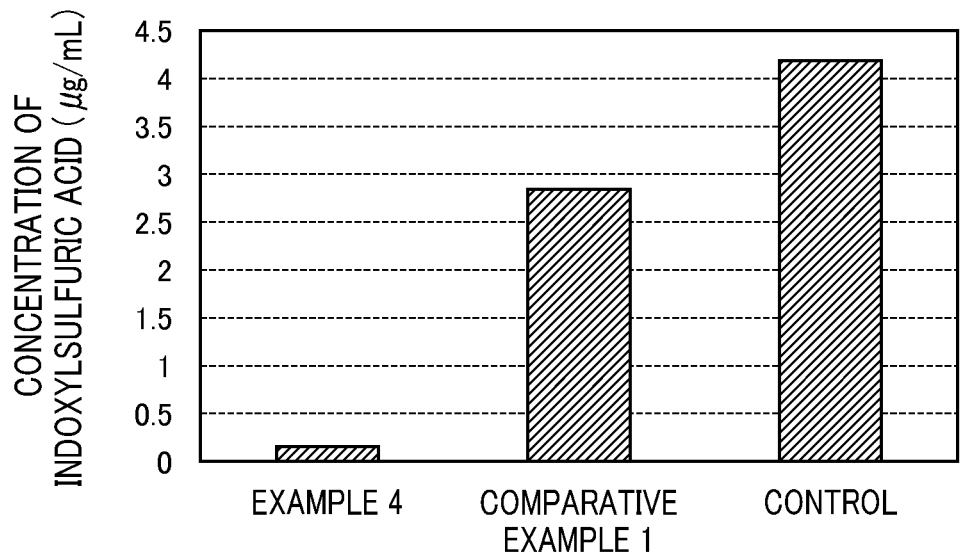
FIG. 3 is a graph showing the results of the adsorption experiments on indoxylsulfuric acid, using the adsorptive carbons according to Example 4 and Comparative Example 1.

The results from the adsorptive carbons according to Example 4 and Comparative Example 1 are shown in FIG. 3. As shown in FIG. 3, for the control, the concentration of indoxylsulfuric acid in the supernatant was 4.1911 μg/mL, whereas with the adsorptive carbon according to Example 4, the concentration of indoxylsulfuric acid in the supernatant was reduced to 0.1866 μg/mL. On the other hand, the adsorptive carbon according to Comparative Example 1 reduced the concentration of indoxylsulfuric acid only to 2.8487 μg/mL. It can be seen from the results that the adsorptive carbon according to Example 4 can more effectively adsorb and remove indoxylsulfuric acid than the adsorptive carbon according to Comparative Example 1.

(Adsorption Experiment on Ammonia)

After 250 mg of the adsorptive carbon were allowed to stand in 1 L of a sample air containing 500 ppm of ammonia for 90 min, 100 ml of the sample air were aspired with a gas detector tube (ammonia gas detector tube No. 3M) from Gastec Corporation, and the concentration of ammonia was determined. In this experiment, an identical but adsorptive carbon-free run was employed as a control, and the measurement was carried out quadruply for the adsorptive carbon and the control, respectively.

Figure 4:
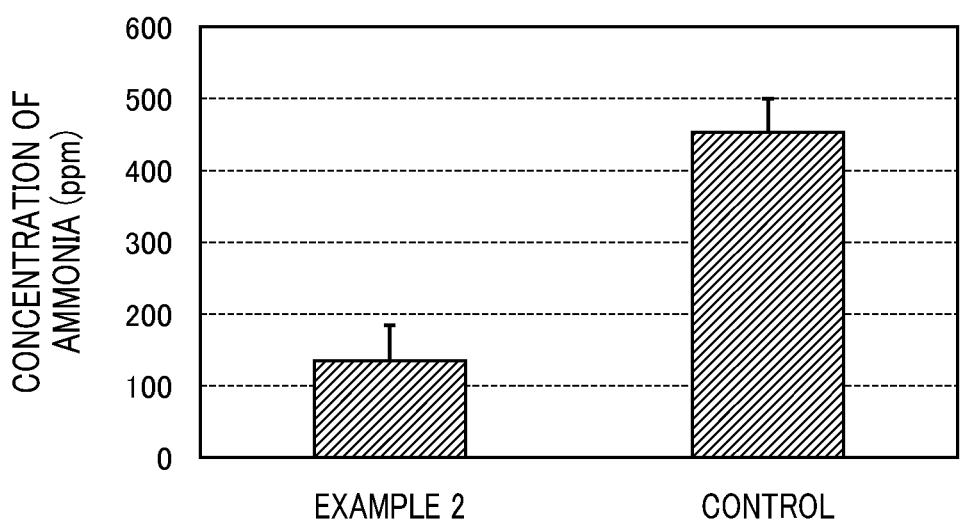
FIG. 4 is a graph showing the results of the adsorption experiments on ammonia, using the adsorptive carbon according to Example 2.

The results from the adsorptive carbon according to Example 2 are shown in FIG. 4. As shown in FIG. 4, for the control sample, the concentration of ammonia was 455±50.0 ppm, whereas with the adsorptive carbon according to Example 2, the concentration of ammonia was reduced to 138±47.9 ppm. It can be seen from the results that the adsorptive carbon according to Example 2 can effectively adsorb and remove ammonia.

INDUSTRIAL APPLICABILITY

The adsorptive carbon of the present invention can effectively adsorb vivotoxins such as advanced glycation end products. Therefore, the use of the adsorptive carbon as an oral adsorbent enables the adsorption of advanced glycation end products and the like thereon in the gastrointestinal organs and the excretion thereof out of the body. From this finding, it is expected that the adsorptive carbon of the present invention can provide the effect of preventing and/or delaying various types of organ disorders not only in renal dysfunction patients but also in metabolic syndrome patients.

In addition, because the gases are not used in the calcination of carbonaceous raw materials, when cellulosic nonwoven fabrics are employed as the carbonaceous raw materials, adsorptive carbons that maintain the respective structures of the original nonwoven fabrics can be obtained. Accordingly, it is expected that the adsorptive carbons thus obtained can be utilized in Double Filtration Plasmapheresis (DFPP) as produced.

The invention claimed is:

1. A method of producing an adsorptive carbon having a total pore volume of 0.10 to 1.0 mL/g, an average pore diameter of 1.0 to 2.0 nm, and an absorbance of an infrared absorption band at 1650-1800 cm−1 of no less than 0.005, the method, comprising a step of obtaining the absorptive carbon by calcinating cellulose with an electric furnace.

2. The method according to claim 1, wherein the cellulose is a high purity cellulose of no less than 90% purity.

3. The method according to claim 1, wherein the cellulose is a cellulose particulate or a cellulosic nonwoven fabric.

4. The method of producing an absorptive carbon according to claim 1, the method consisting of a step of obtaining the absorptive carbon by calcinating the cellulose with an electric furnace.

* * * * *